(12) United States Patent
Schwank et al.

(10) Patent No.: US 9,370,707 B2
(45) Date of Patent: Jun. 21, 2016

(54) ADAPTIVE MOUTH GUARD AND METHOD OF USE

(71) Applicant: Akervall Technologies, Inc., Ann Arbor, MI (US)

(72) Inventors: Johann Schwank, Ann Arbor, MI (US); Valarie Thomas, Ann Arbor, MI (US); Jan Akervall, Ann Arbor, MI (US)

(73) Assignee: Akervall Technologies, Inc., Ann Arbor, MI (US)

(*) Notice: Subject to any disclaimer, the term of this patent is extended or adjusted under 35 U.S.C. 154(b) by 0 days.

(21) Appl. No.: 14/682,326

(22) Filed: Apr. 9, 2015

(65) Prior Publication Data
US 2015/0328526 A1    Nov. 19, 2015

Related U.S. Application Data (60) Provisional application No. 61/992,298, filed on May 13, 2014.

(51) Int. Cl.
*A63B 71/08*    (2006.01)
*A61C 5/14*    (2006.01)

(52) U.S. Cl.
CPC .............. *A63B 71/081* (2013.01); *A61C 5/14* (2013.01); *A63B 71/085* (2013.01)

(58) Field of Classification Search
CPC .................................................. A63B 71/081
USPC ............... 433/215, 27, 80, 82, 88, 34, 37–38
See application file for complete search history.

(56) References Cited

U.S. PATENT DOCUMENTS

| | | | |
|---|---|---|---|
| 3,532,091 A * | 10/1970 | Lerman | A63B 71/085 128/861 |
| 5,082,007 A | 1/1992 | Adell | |
| 7,226,878 B2 | 6/2007 | Wagner et al. | |
| 7,498,276 B2 | 3/2009 | Wagner et al. | |
| 7,825,045 B1 | 11/2010 | Wagner et al. | |
| 8,087,101 B2 | 1/2012 | Ferguson | |

(Continued)

FOREIGN PATENT DOCUMENTS

| CA | 2649179 C | 4/2013 |
|---|---|---|
| DE | 202007016030 U1 | 4/2008 |

(Continued)

OTHER PUBLICATIONS

European Patent Office; International Search Report and Written Opinion of the International Searching Authority, Jul. 6, 2015, issued in PCT/US2015/027693; EPO, Rijswijk, Netherlands; EPO Munich, Germany.

*Primary Examiner* — Victoria J Hicks
*Assistant Examiner* — Tarla Patel
(74) *Attorney, Agent, or Firm* — Marshall & Melhorn, LLC (57) ABSTRACT

A dental appliance is disclosed designed to protect a wearer's dentitions against injury from impacts suffered in sports or other activities that can cause chipping, fracturing, dislodging or evulsion of teeth. The appliance may be custom-fittable with at least one pocket having an energy absorbing fluid. The energy absorbing fluid be nanosuspensions of small particles in viscous fluids that can undergo shear thickening when the dental appliance is struck by an object. The appliance dampens and diffuses horizontal and axial forces and directs them away from dentitions thereby reducing the risk for dental injuries.

6 Claims, 4 Drawing Sheets

(56) References Cited

U.S. PATENT DOCUMENTS

| | | |
|---|---|---|
| 8,100,131 B2 | 1/2012 | Swann et al. |
| 8,510,863 B2 | 8/2013 | Ferguson |
| 8,739,316 B1 | 6/2014 | Norton |
| 8,894,594 B2 | 11/2014 | Pflaster et al. |
| 2007/0084471 A1 | 4/2007 | Napoli et al. |
| 2011/0242746 A1 | 10/2011 | Hoffman et al. |
| 2012/0085355 A1 | 4/2012 | Swann et al. |
| 2013/0068236 A1 | 3/2013 | Lovat |
| 2013/0338554 A1 | 12/2013 | Pflaster et al. |
| 2013/0338555 A1 | 12/2013 | Pflaster et al. |
| 2014/0148746 A1 | 5/2014 | Pflaster et al. |
| 2015/0013039 A1 | 1/2015 | Parker et al. |

FOREIGN PATENT DOCUMENTS

| | | |
|---|---|---|
| EP | 2004298 B1 | 10/2009 |
| EP | 2174978 A1 | 4/2010 |
| EP | 2482942 B1 | 1/2014 |
| JP | H05-023353 A | 2/1993 |
| WO | 2007/116213 A1 | 10/2007 |
| WO | 2009142491 A1 | 11/2009 |
| WO | 2011036466 A1 | 3/2011 |
| WO | 2013045892 A1 | 4/2013 |
| WO | 2013132212 A1 | 9/2013 |

* cited by examiner

ADAPTIVE MOUTH GUARD AND METHOD OF USE

RELATED APPLICATIONS

This application claims priority to and the benefit of U.S. Provisional Application Ser. No. 61/992,298 filed on May 13, 2014, which is incorporated by reference herein.

FIELD OF THE INVENTION

An adaptive mouth guard to protect the dentition of people engaged in various sports, dentistry, hospital, or military activities. The adaptive mouth guard has a thermoplastic polymer structure that incorporates a shear thickening fluid to absorb energy.

BACKGROUND OF THE INVENTION

There is mounting evidence that the materials typically used in mouth guards do not provide adequate protection. Despite widespread use of mouth guards in sports, there are more than one million dental injuries per year, and dental injuries are the most common type of orofacial injuries in sports.

According to the American Dental Association (ADA), the lifetime costs for treatment of serious dental injuries are $15,000-$20,000 per tooth. Individuals who damage a tooth end up with multiple visits to the dentist, with down stream periodontal disease or other dental problems often leading to the need for implants. This brings the annual cost for dental injuries in sports in the USA alone to $500 million.

Dental injuries are also quite common in hospitals during transoral proceedures. By way of example, a transoral proceedure may be such as, but not limited to, an intubation or a rigid or flexible endoscopic procedure.

Dental injuries during transoral procedures affect approximately 1% of patients, which corresponds to 150,000 patients/year and an annual cost of $75 million. Furthermore, dental injuries during intubation are the leading reason for litigation against anesthesiologists.

Inexpensive mouth guards tend to have a poor fit, leading to low compliance of mouth guard use. Professional-grade mouth guards require fitting by dentists, making the mouth guards very expensive; but even these professional-grade mouth guards tend to be bulky, and restrict breathing and verbal communication.

Since typical mouth guards are so uncomfortable, athletes frequently take them out and put them back in. The repeated handling of saliva-coated mouth guards leads to contamination of mouth guards from hands and fingers with pathogens.

Clearly, a better mouth guard is needed that is thin enough so that does not impede breathing and communication, and does not tempt athletes to frequently remove it, while providing a much higher degree of protection than the state-of-the-art.

There are sports activities where high-velocity impact events occur that reach peak force very quickly, within milliseconds (e.g. getting hit by an ice hockey stick or puck). While in other sports such as skateboarding, a crash can lead to landing on the chin or cheek. The peak force resultant from such an impact will be lower, but applied over a larger area of the face.

In medical applications, such as intubation of patients during surgery, the peak forces are reached even more slowly but maintained over extended time periods, i.e. by laryngoscopes and rigid endoscopes inserted into the patient's mouth and throat. Similarly, in bruxism (night time teeth grinding), the forces are applied primarily in specific locations within the dental region, in the rear of the mouth in the molar region.

A variety of materials have been used for mouth guards, including polyvinylacetate-polyethylene or ethylene vinyl acetate copolymer (EVA), latex rubber, polyurethane, polyvinylchloride, and acrylic resin. The current paradigm in materials selection for commercially available, inexpensive mouth guards is based on the concept that soft materials, such as ethylene vinyl acetate (EVA), provide protection by cushioning the teeth upon impact. However, in order to achieve the required degree of protection, relatively thick layers of polymer have to be used, with typical thicknesses in the range of 4 mm since these materials are highly compressible and thus tend to "cave in" and deform under impact. These mouth guards also usually fit very poorly.

Better fitting, professional-grade mouth guards can be made from harder acrylic resins. This usually requires a visit to the dentist, where impressions are taken, so that the mouth guard can be fabricated in a dental laboratory. This process is time consuming and costly, a major impediment to consumer acceptance.

Conventional mouth guards require the users to bite down on the mouth guards to keep them in place. The approximately 4 mm thickness of conventional mouth guards makes it almost impossible to wear them on both the upper and lower teeth. Furthermore, since the mouth guards are so bulky, they hinder breathing and verbal communication. It is also almost impossible to drink with the mouth guard in place.

For sports where very high impact energies and velocities may be encountered, and for clinical applications where high stresses are encountered when intubation laryngoscopes and endoscopic instruments inserted into the throat apply pressure on the teeth, it is necessary to develop a much stronger mouth guard that can more effectively dissipate the forces.

SUMMARY OF THE INVENTION

A dental appliance may have one or more flaps and/or cusps. A bite line extends through the appliance for receiving dentition. A least one pocket for a shear thickening fluid is located in the appliance.

BRIEF DESCRIPTION OF THE DRAWINGS

The features of the device and method of using it will be better understood in the context of the detailed description in conjunction with the drawings in which.

DETAILED DESCRIPTION OF THE INVENTION

It is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions, directions or other physical characteristics relating to the embodiments disclosed are not to be considered as limiting, unless the claims expressly state otherwise.

Figure 1:
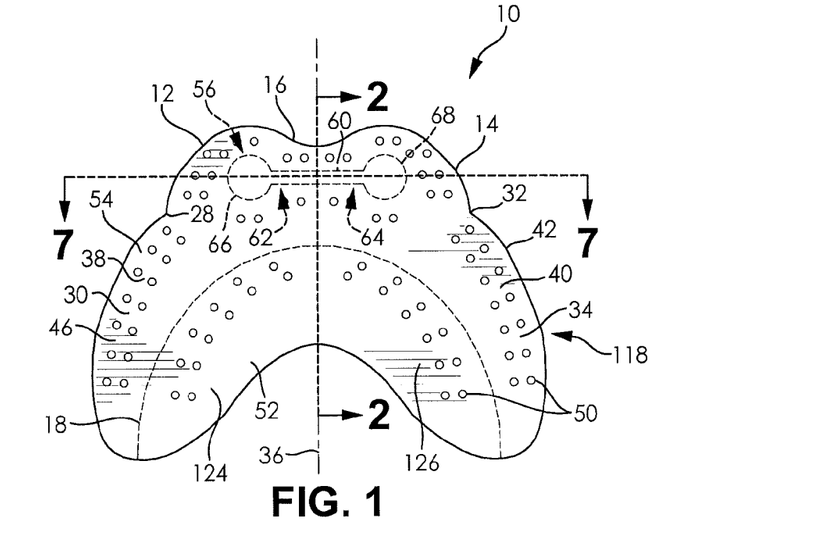
FIG. 1 depicts a top view of one embodiment of a dental appliance in a first condition.

Turning now to FIG. 1, one embodiment of a dental appliance 10 is depicted. A preferred embodiment of the dental appliance 10 is shown in a flattened, first state. The appliance 10 is a one-piece, unitary and integrally formed sheet of material. In one embodiment, the appliance 10 may be 0.25 mm to 2 mm thick and fabricated from a polycaprolactone thermoplastic matrix material. Such a material is widely available, inexpensive and readily disposable when the appliance 10 is exhausted.

The appliance 10 may be produced by injection molding, but other production methods are permissible. In one embodiment, the appliance 10 may be produced by 3-D printing. Alternatively, a portion of the appliance 10 may be injected molded and another portion produced by 3-D printing.

The appliance 10 comprises a first front flap 12 and a second front flap 14, which together are called a maxillary flap. A forward cusp 16 is located between the two flaps 12, 14. The cusp 16 extends inwardly into the appliance 10 at least partially dividing the first front flap 12 and the second front flap 14. The cusp 16 extends inwardly toward, but preferably does not reach, a bite line 18.

Figure 9:
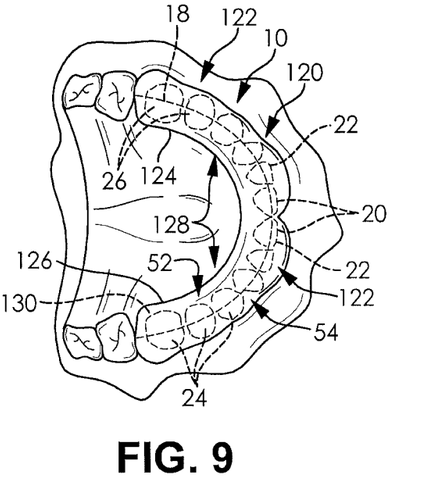
FIG. 9 depicts the dental appliance of FIG. 1 installed on the dentition of a patient.

The bite line 18 is the line on the appliance 10 along which the incisal edges 20 of the incisors 22 and the tips of the occluding surfaces 24 of the posterior teeth 26 come in contact with the appliance 10, as shown in FIG. 9. Together, these edges 20 and surfaces 24 are called crowns herein. The bite line 18 is generally arch-shaped to be complementary to the arrangement of teeth in a wearer's mouth.

A first side cusp 28 further defines the first front flap 12. The first side cusp 28 is located between the first front flap 12 and a first outer side flap 30. The first side cusp 28 extends inwardly into the appliance 10 toward the bite line 18. The first side cusp 28 may extend inwardly into the appliance 10 at the same depth as the forward cusp 16 or to a greater or lesser extent.

A second side cusp 32 further defines the second front flap 14. The second side cusp 32 is located between the second front flap 14 and a second outer side flap 34. The second side cusp 32 extends inwardly into the appliance 10 toward the bite line 18. The second side cusp 32 may extend inwardly into the appliance 10 at the same depth as the forward cusp 16 or to a greater or lesser extent.

In the embodiment depicted in FIG. 1, a line of symmetry 36 extends from the forward cusp 16 to equally divide the appliance 10 into a first half 38 and a second half 40, which are symmetric with one another. More particularly, the line of symmetry 36 results in a mirror image between the first half 38 and the second half 40. It is permissible, however, for the first half 38 to be non-symmetrical with the second half 40.

Figure 10:
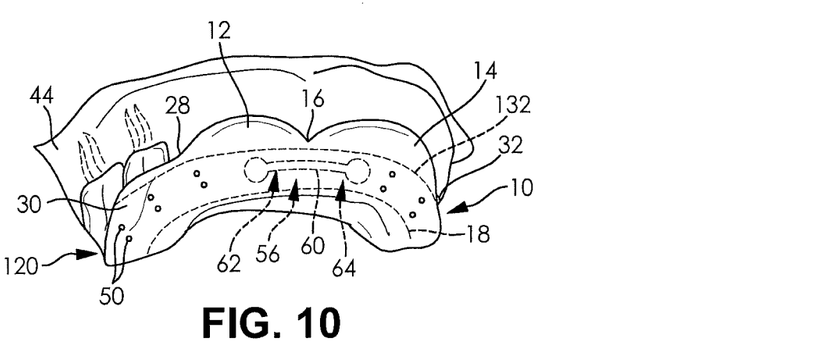
FIG. 10 depicts another view of the dental appliance of FIGS. 1 and 9 installed on the dentition of a patient.

A perimeter 42 defines the first front flap 12, the second front flap 14, and the side flaps 30, 34. The perimeter 42 is preferably rounded, or curvilinear. This embodiment is envisioned to impose the least, if any, discomfort to the wearer of the dental appliance 10 since it has no sharp corners or edges to embed into the soft gum tissue 44, as shown in FIG. 10.

The appliance 10 has a first planar side 46 and a second planar side 48 in the first state. The second planar side 48 is opposite the first planar side 46. The second planar side 48 may be parallel to the first planar side 46. Therefore, in the depicted embodiment, the appliance 10 has a substantially constant thickness, except where otherwise noted in the discussion below. The appliance 10 may, however, not have a substantially constant thickness.

For example, the entire thickness of the appliance 10 may be increased, or it may be increased in certain areas. 3-D printing may be used to increase the thickness of the appliance 10 to 1.6-3 mm by depositing a polycaprolactone matrix on top of an existing layer.

Figure 7:
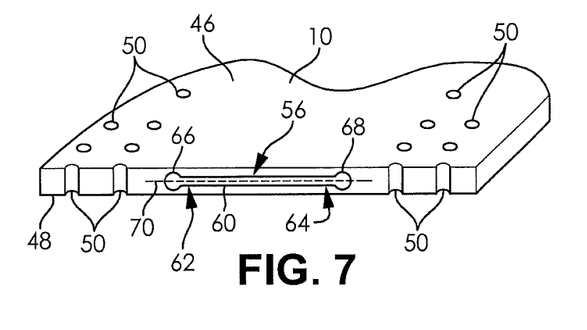
FIG. 7 is a sectional view through another embodiment of a dental appliance.

The appliance 10 depicted in FIG. 1 has a plurality of open spaces 50 on an inner portion 52 and an outer portion 54 of the bite line 18. The open spaces 50 extend through the appliance 10 from the first side 46 to the second side 48, as shown in FIG. 7.

The open spaces 50 are depicted as cylindrical with circular cross-sections, however, it can be appreciated that other shapes, numbers, designs and/or orientations are permissible. It is preferred that regardless of the open spaces 50 selected, that the design selected is symmetrical about the line symmetry 36, but it is not required.

Figure 2A:
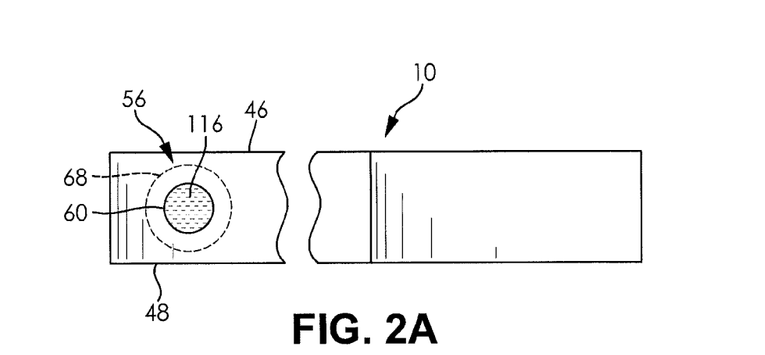
FIG. 2A depicts a cross-section along line 2-2 from FIG. 1.

FIGS. 1 and 2A depict one embodiment of a pocket 56 located within the appliance 10. In the depicted embodiment, the pocket 56 is located between the first planar side 46 and the second planar side 48 of the appliance 10. In FIG. 1, the pocket 56 is located between the bite line 18 and the outer perimeter 42. The pocket 56 may be entirely encased within the appliance 10, as depicted in FIGS. 1 and 2A.

Figure 2B:
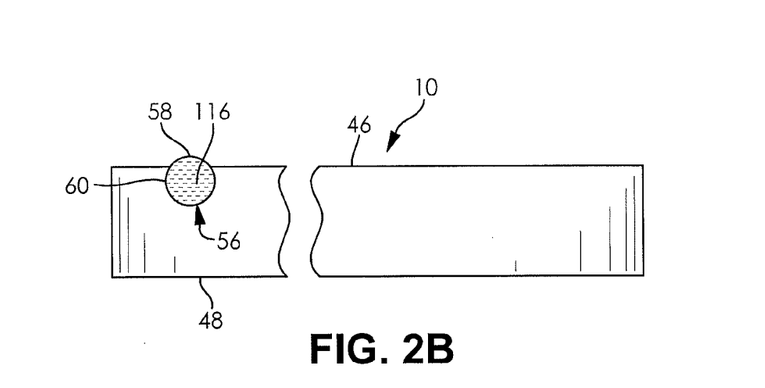
FIG. 2B depicts an alternative embodiment to the cross-section depicted in FIG. 2A.

In an alternative embodiment, a portion of the pocket, or the entire pocket, may be exposed. FIG. 2B depicts one portion 58 of the pocket 56 extending above the first planar side of the appliance 10. While FIG. 2B depicts the portion 58 extending from the first planar side to be a fraction of the pocket 56, larger portions of the pocket 56 can be exposed. Additionally, while FIG. 2B depicts a portion 58 of the pocket 56 extending from the first planar side 46, it is possible for the pocket 56 to extend from the second planar side 48 lower surface while not extending from the first planar side 46 or for the pocket 56 to extend from both sides 46, 48. Further yet, it is permissible for two or more portions 58 of the same pocket 56 to extend from the appliance 10 or for two or more portions of different pockets to extend from the appliance 10. Each of the alternatives discussed above is not limited to the embodiments discussed so far, but applies equally to each embodiment discussed herein.

In the embodiment depicted in FIGS. 1 and 2A, the pocket 56 comprises a channel 60 extending transverse to the line of symmetry 36. The channel 60 is depicted a having a circular cross section, but other cross sections are permissible. Further, while the figures depict the channel 60 having the same cross-section, the shape and size of the channel 60 can change along its course.

The channel 60 preferably extends from the first front flap 12 to the second front flap 14. The channel 60 has a first end portion 62 and a second end portion 64. In the depicted embodiment, the first end portion 62 is connected to a first reservoir 66 and the second end portion 64 is connected to a second reservoir 68.

In FIG. 1, the reservoirs 66, 68 are depicted as spherical; however, other shapes and sizes are permissible. What is preferable is that the reservoirs 66, 68 are in fluid communication with the channel 60, regardless of the shape of the channel 60 or the reservoirs 66, 68.

FIG. 1 depicts the reservoirs 66, 68 in the first front flap 12 and the second front flap 14 of the appliance 10. More particularly, the reservoirs 66, 68 are symmetrically located with respect to one another and axially aligned with the channel 60. As shown in FIG. 7, the reservoirs 66, 68 are centered on an axis 70 of the channel 60 so that the channel axis 70 bisects the reservoirs 66, 68.

While FIG. 1 depicts two reservoirs 66, 68, only a single reservoir can be used. Further yet, it is conceivable that no reservoir is required at all. It is also within the scope of the disclosure that the single or more than one reservoir can be located in a position other than at an end portion 62 or 64 of the channel 60. By way of example, the reservoir might be located equally between the two end portions 62 or 64, or at any other location between the two end portions 62, 64.

Figure 3A:
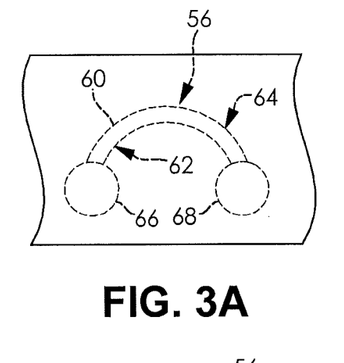
FIG. 3A is a top view of one embodiment of a pocket of a dental appliance.

FIG. 3A depicts an alternative pocket 56 design wherein the channel 60 is curved, such as in a convex shape. Reservoirs 66, 68 are located at the end portions 62, 64 of the convex shape.

Figure 3B:
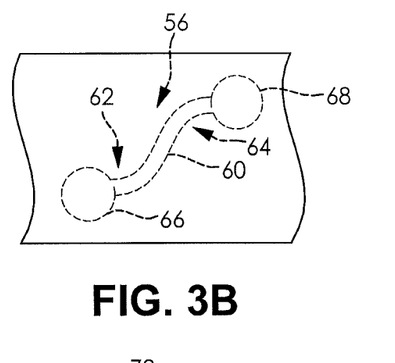
FIG. 3B is a top view of another embodiment of a pocket of a dental appliance.

FIG. 3B depicts yet another pocket 56 design wherein the channel 60 has a serpentine trajectory. Reservoirs 66, 68 are located at the end portions 62, 64 of the channel 60.

Figure 3C:
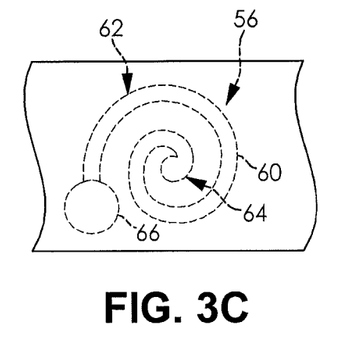
FIG. 3C is a top view of another embodiment of a pocket of a dental appliance.

FIG. 3C depicts a coiled channel 60 design. In this embodiment, the channel 60 begins at a central point 72 and extends radially outward from the central point 72 in a curlicue fashion so that one portion of the channel 60 is radially encircled by another portion of the channel 60. A reservoir is located at the outermost end of the channel.

Figure 3D:
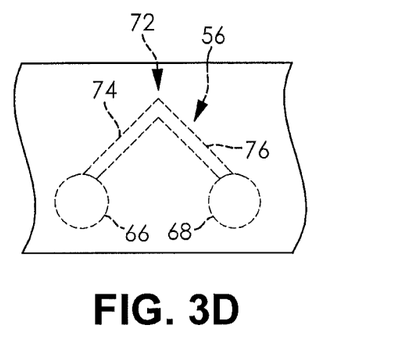
FIG. 3D is a top view of another embodiment of a pocket of a dental appliance.

FIG. 3D depicts yet another design wherein the pocket comprises a first and second channel 74, 76 angled with respect to one another. The first and second channels 74, 76 may be substantially linear. The channels 74, 76 intersect one another at a point and are in fluid communication with one another. Reservoirs 66, 68 are located at the ends of the channels 74, 76 opposite the intersection point.

Figure 4:
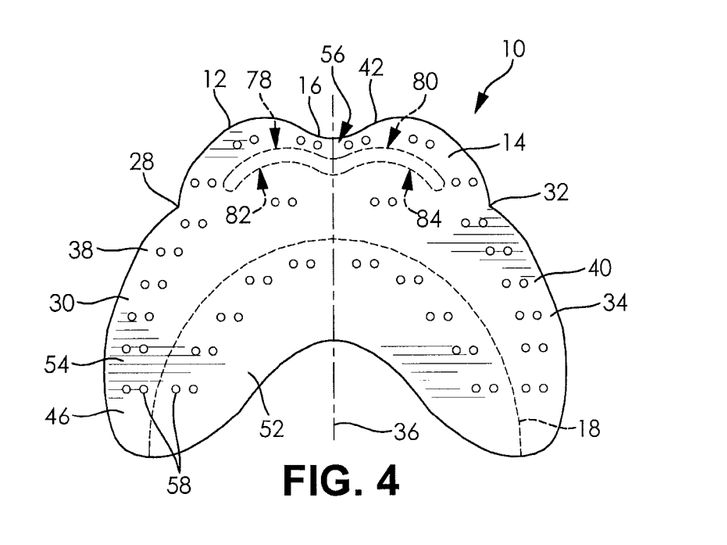
FIG. 4 is a top view of another embodiment of a dental appliance.

FIG. 4 depicts another pocket design wherein the pocket 56 has a complementary shape to the outer perimeter 42 of the appliance 10. More particularly, the pocket 56 has a first portion 78 located in the first front flap 12. The first portion 78 is located inward from the outer perimeter 42 but tracks the shape of the outer perimeter 42. More particularly, the first portion 78 has a convex shape.

The pocket 56 also has a second portion 80 located in the second flap 14. The second portion 80 is symmetric with the first portion 78. The second portion 80 is located inward from the outer perimeter 42 but tracks the shape of the outer perimeter 42 also with a convex shape.

Inboard portions 82, 84 of the first portion 78 and the second portion 80 angle radially inwardly into the appliance 10 and meet at the line of symmetry 36 of the appliance 10. The inboard portions 82, 84 are complementary to the shape of the forward cusp 16.

Figure 5:
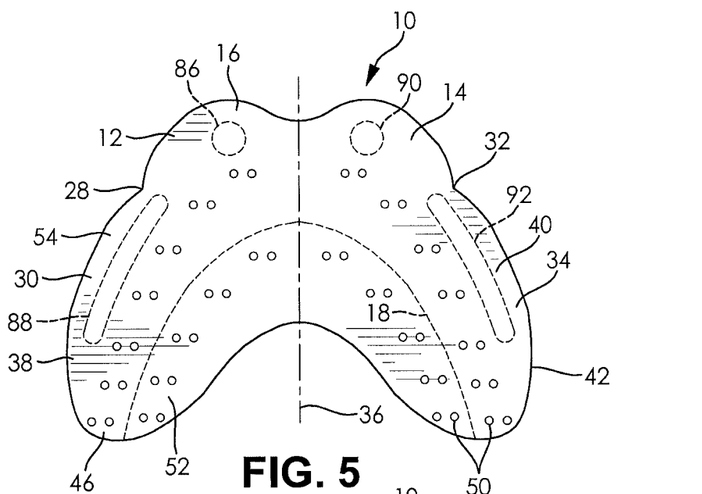
FIG. 5 is a top view of another embodiment of a dental appliance.

FIG. 5 depicts another embodiment with four pockets. A first pocket 86 has a round cross-section and is located in the first front flap 12. A second pocket 88 has a tubular cross section and is located in the first outer side flap 30. The second pocket 88 extends along, but inboard of, the outer perimeter 42 of the first outer side flap 30. The first and second pockets 86, 88 are located in the first side 38 of the appliance 10.

The second side 40 of the appliance 10 is symmetrical with the first side 38. Namely, a third pocket 90 with a round cross section is provided in the second front flap 14. A fourth pocket 92 with a tubular cross section is located in the second outer side flap 34 along, but inboard of, the outer perimeter 42.

In the embodiment depicted in FIG. 5, the pockets 86, 88, 90, 92 are not in fluid communication with one another. However, one or more of the pockets 86, 88, 90, 92 may be in fluid communication with one another.

Figure 6:
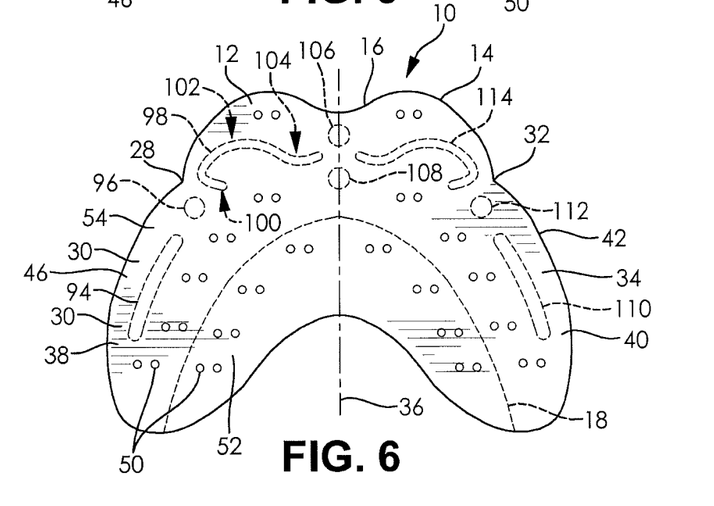
FIG. 6 is a top view of another embodiment of a dental appliance.

FIG. 6 depicts another embodiment wherein on the first side 38 of the appliance 10, a first pocket 94 with a tubular cross section extends along, but inboard of, the outer perimeter 42 in the first outer side flap 30. A second pocket 96 having a circular cross section is located adjacent the first side cusp 28. A third pocket 98 is located inboard of the outer perimeter 42 in the first front flap 12. The third pocket 98 may have a first portion 100 that curls radially inwardly into the appliance 10. A second portion 102 of the third pocket 98 extends radially outward toward the outer perimeter 42 in an arch-shaped fashion. A third portion 104 of the third pocket 98 extends radially inwardly away from the outer perimeter 42 but in a complementary fashion to the outer perimeter 42 of the first front flap 12 and the forward cusp 16.

Radially inward from the forward cusp 16, a fourth pocket 106 is provided. The fourth pocket 106 has a circular cross section. A fifth pocket 108 is provided radially inward of the fourth pocket 106. The fifth pocket 108 has a circular cross section.

The appliance 10 has a sixth pocket 110 as a mirror image to the third pocket 98, a seventh pocket 112 as a mirror image to the second pocket 96 and an eighth pocket 114 as a mirror image to the first pocket 94. The sixth 110, seventh 112 and eighth 114 pockets are located on the second side 40 of the appliance 10.

In the embodiment depicted in FIG. 6, the pockets 94-114 are not in fluid communication with one another. However, one or more of the pockets 94-114 may be in fluid communication with one another.

Turning now to FIG. 7, the open spaces 50 extending through the appliance 10 from the first planar side 46 to the second planar side 48 can be appreciated. The open spaces 50 are shown to have circular openings at the sides 46, 48, however, other shapes of the open spaces 50 are permissible. Further, while FIG. 7 depicts the open spaces 50 having all the same size and shape, it can be appreciated that the size and shape of the open spaces 50 can vary. Continuing with the depicted appliance 10 in FIG. 7, the open spaces 50 extend through the appliance 10 with a cylindrical cross section. The opens spaces 50 in FIG. 7 are in in the condition where a force has not been applied to the appliance 10.

A fluid 116 is located in one or more of the pockets (for example pocket 56) of the various embodiments described above. The fluid 116 in the pockets may all be the same or it may be different. Preferably, if a fluid 116 is provided in a pocket is comprises an energy absorbing fluid. The energy absorbing fluid may be such as a shear thickening fluid comprised of a suspension of nanoparticles inside a polymer matrix.

Colloidal suspensions of nanoparticles have a natural resistance to flow due to random collisions between the particles. A high velocity impact onto the appliance 10 that is filled with nanoparticles suspended in a fluid imposes shear forces on the particles. When the shear rate increases beyond a certain threshold value, the viscosity of the fluid increases suddenly due to hydrodynamic interactions between particles that lead to transient fluctuations in particle concentration and the formation of so-called hydroclusters. The viscosity increases in a matter of milliseconds after receiving a force and causes the appliance 10 to stiffen.

Typical separation distances between particles in these hydroclusters are in the range of nanometers. The onset of shear thickening is related to the size of the submicron particles and their volume fraction in the suspension. The onset of shear thickening can be modified by changing not only the particle size, but also the particle surface structure and chemical functionality. Surface roughness plays an important role, and the surface of particles can be further modified by adsorption of ions, surfactants, and polymers. During the shear-thickening event, a significant amount of impact energy is dissipated as the fluid stiffens, and within a few seconds after the event, the fluid returns to its original liquid like state.

The shear-thickening event consumes energy as the structure of the nanofluid changes, and the stiffening of the entire structure dissipates a significant amount of the impact energy without transmitting it to the user's dentition. Furthermore, the energy absorption can be tuned for a given range of impact energies by modification of the composition of nanofluids. The tuning of the nanofluid properties is based on the following principles: In the shear thickening range of Brownian suspensions, the slope of the viscosity-shear rate curve tends to increase as the solid particle volume fraction increases. The onset of shear thickening of a nanosuspension occurs at a universal value of the Peclet number, Pe:

$$Pe = \frac{\eta_s \gamma a^3}{k_B T} \propto \gamma t_D$$

where $\eta_s$ is the viscosity of the suspending fluid, $\gamma$ the shear rate, a the radius of the solid particles, $k_B$ the Boltzmann constant, T the absolute temperature, and $t_D$ the time for a particle to diffuse a distance equal to is radius a. From this, the critical shear rate for the onset of shear thickening can be deduced to be proportional to the inverse of the cube of the particle radius.

Additional tuning of the properties can be achieved through electrostatic charges and deformations of the steric stabilizing layer that can become important when small particles are mixed into a fluid. Therefore, particles with long-ranged repulsive interparticle potentials are expected to be most shear thickening. This opens the opportunity to modify the repulsive interparticle potentials by chemically functionalizing the surface of the particles with epoxy groups, hydroxyl groups, carboxyl groups, or amino groups. By changing variables such as particle type, particle size, surface functional groups, and particle/fluid weight ratio, it is possible to tune the range where the mouth guard responds dynamically and stiffens up for a given sport or military or medical application, where very different ranges of impact energies and velocities of impacting objects are encountered.

One embodiment uses non-Newtonian fluids that are chemically compatible with thermoplastic polymers, and incorporates the fluids into internal cavities or small channels in a thermoplastic polymer matrix. Non-Newtonian fluids are fluids whose viscosity (a measure of a fluids resistance to deformation by shear or tensile stresses) is dependent on the shear rate. Examples of such fluids are salt solutions, starch suspensions, and molten polymers.

Another embodiment of the invention uses shear-thickening solid liquid suspensions that exhibit increased viscosity when exposed to shear forces. Examples of such solid/liquid suspensions are:

a) submicron-size silicon oxide particles in USP grade polyethylene glycol (PEG);

b) submicron-size colloidal silicon oxide particles in USP grade glycerin;

c) silicon nanoparticles in USP grade glycerin;

d) silicon nanoparticles in USP grade polyethylene glycol (PEG);

e) silicon dioxide nanoparticle in singular or binary mixtures in polyethylene glycol (PEG 200 and PEG 400);

f) silicon dioxide nanoparticles functionalized with linear hydrocarbons in singular or binary mixtures in polyethylene glycol (PEG 200 and PEG 400);

g) silicon dioxide nanoparticles functionalized with silanes in singular or binary mixtures in polyethylene glycol (PEG 200 and PEG 400);

h) bentonite or kaolin clay ($Al_2Si_2O_7$) particles in USP grade glycerin;

i) bentonite or kaolin clay ($Al_2Si_2O_7$) particles in USP grade polyethylene glycol (PEG);

j) polycaprolactone particles in USP grade polyethylene glycol (PEG);

k) salt solutions;

l) starch suspensions; and/or m) molten polymers.

In addition to these examples, many other solid particle-liquid combinations can be used to achieve shear thickening behavior. Depending on the shear rate and the amount of shear force, these suspensions can stiffen and thereby increase the energy absorption ability of the mouth guards by diverting the impact energy into the fluid filled cavities and channels and directing the impact forces away from the dentition. When the shear stress is removed, the nanosuspension inside the appliance returns to its original, non-shear thickened state with lower viscosity, making the appliance again comfortable to wear.

The pockets inside the thermoplastic polymer matrix are filled with nanosuspensions that are tuned to exhibit a maximum dynamic response at a given trigger impact force. Tunable response where impact energies of different magnitudes can be dissipated can be achieved by incorporating nanosuspensions formulated with nanoparticles functionalized with linear hydrocarbons or with silanes. A range of nanosuspensions may be used that undergo shear thickening in dynamic response to peak forces and shear rates analogous to an impact event characteristic to a given activity or anticipated force(s).

The pockets may also be filled with force dampening fluids such as glycerin and polyethylene glycol that do not undergo shear thickening.

A method of using the dental appliances described above to protect the dentition of a wearer follows. The following description will use the embodiment of FIG. 1, but it can be appreciated that the method is readily used with the other embodiments.

The appliance 10 is initially in a first planar state 118, as shown in FIG. 1. At room temperature, the appliance 10 is rigid. The appliance 10 may be heated such as by convection, conduction and/or radiation until it is pliable. Once pliable, the appliance 10 is located adjacent the dentition of a patient. In the preferred embodiment, the appliance 10 is located adjacent the maxilla (upper dentation) into a second, non-planar state 120 described below, and depicted in FIGS. 9, 10 and 11. Alternatively, the appliance 10 may be located adjacent the mandible (lower jaw), or a first sheet can be located adjacent the maxilla and a second sheet can be located adjacent the mandible.

Continuing with the embodiment wherein the appliance 10 is located just adjacent the maxilla, the crowns of the dentition 20, 24 are positioned adjacent the bite line 18 on the appliance 10. The appliance 10 is moved into contact with the dentition 20, 24 and then molded around the dentition 20, 24. More particularly, the first and second front flaps 12, 14 are molded in front of the outward facing surfaces 122 of the dentition. Similarly, the outer side flaps 30, 34 are molded in front of the outward facing surface 122 of the dentition. Preferably, the first and second front flaps 12, 14, and also the outer side flaps 30, 34, are located vertically, or with a small angle variance from vertical (e.g. 10 degrees), from the bite line 18. In other words, the flaps 12, 14, 30, 34 are located parallel, or approximately parallel, the outward facing surfaces 122. The flaps 12, 14, 30, 34 are preferably located in this orientation because it minimizes the mobility of at least the central incisor teeth 22 when the tips of these teeth 22 are subjected to a force.

The appliance 10 also comprises a first inner side flap 124 and a second inner side flap 126. The flaps 124, 126 are bounded by the perimeter 42 and the bite line 18. As shown in FIG. 1, the flaps 124, 126 are symmetrical across the line of symmetry 36, but non-symmetrical flaps are permissible.

The first inner side flap 124 and the second inner side flap 126 are molded upwardly so they are positioned behind rearward facing surfaces 128 of the dentition. The flaps 124, 126 are located vertically, or within a small angle variance from vertical (e.g. 10 degrees) from the bite line 18. In other words, the flaps 124, 126 are located parallel, or approximately parallel, the rearward facing surfaces 128.

Figure 11:
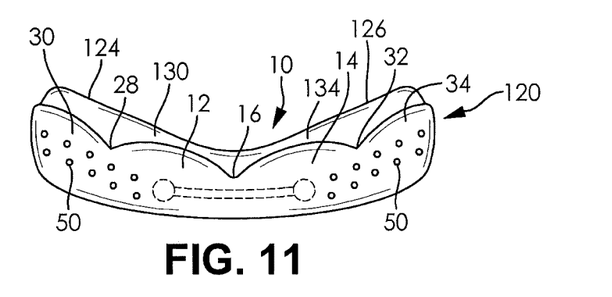
FIG. 11 depicts the dental appliance of FIG. 1 in a second condition.

The upward location of the flaps 12, 14, 30, 34, 124, 126 effectively encases the outward and rearward surfaces 122, 128 of the maxilla dentition in a channel 130, which can be appreciated from FIGS. 9 and 11. The channel 130 is curved along the bite line 18 so as to be complimentary to the wearer's dentition. The channel 130 protects the outward and inward facing surfaces 122, 128 as well as the incisal edges 20 and occluding surfaces 24 of many of the wearer's dentition.

When the appliance 10 is fit onto the dentition of a wearer, the forward cusp 16 falls centrally between the two maxillary central incisor teeth 22. When formed to the dentitions, the first and second front flaps 12, 14 cross over a maxillary teeth-gum intersection line 132 and extend over the soft gum tissue 44, as shown in FIG. 10. It has been found that when the appliance 10 extends over the maxillary teeth-gum intersection line 132, the appliance 10 more robustly can protect the dentition from being moved during force application. In one embodiment, the flaps 12, 14 extend beyond the teeth-gum intersection line 132 approximately 0.25 to 0.35 mm. While one range of extension is mentioned above, it can be appreciated that this dimension can be larger or smaller to cover more or less of the soft gum tissue 44.

The flaps 12, 14, 30, 34, 124, 126 can be manually manipulated to position them as described above. In addition, the wearer can draw air through the open spaces 50. The vacuum created by the wearer by drawing the air through the spaces 50 pulls the pliable appliance 10 into conformal contact with the dentition.

The manual manipulation and/or the vacuum applied to the appliance 10 causes an interior surface 134 of the appliance 10 to mold into intimate contact with the outward facing surfaces 122 and/or rearward facing surfaces 128 of the dentition. As the appliance 10 cools, it may shrink into further contact with the dentition. During cooling, the appliance 10 hardens into a shape that well adheres to the contours of every unique tooth. This adherence ensures the appliance 10 does not become dislodged. In addition, the adherence and thin dimension of the appliance 10 provides a clear, unobstructed view of the wearer's mouth, voice box and trachea.

The open spaces 50 in the appliance 10 provide a conformal fit of the appliance 10 onto any dentition and enable a secure custom fit by changing in size and in shape in all or some when the appliance 10 is in the pliable condition. The secure, custom fits enables the appliance to remain fixed on the dentition. The open spaces 50 allow the softened thermopolymer material to be formed into a three-dimensional shape without buckling, bunching, creasing, or bulging.

If the appliance 10 has to be re-fitted after it has cooled and hardened, it can be warmed to its softening point and the fitting process can be repeated because its second state is only a semi-permanent state.

Figure 8:
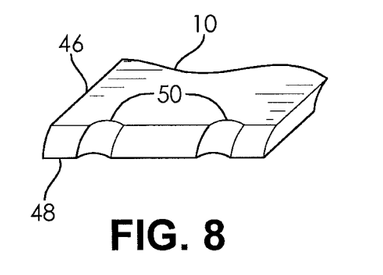
FIG. 8 depicts a force being applied to the dental appliance of FIG. 7.

FIG. 8 depicts two of the open spaces 50 of FIG. 7 but subject to a force. The force deforms the open spaces 50 resulting in dissipation of the force. In FIG. 8, the open space 50 is deformed as a result of one kind of force from a circular cross-section to an oval cross-section. The shape change of the open spaces 50 expends some or all of the energy of the force traveling through the appliance 10.

In one example, because the appliance 10 maintains a constant volume, when a force encounters an open space 50, the deformed open space 50 compresses the adjacent open spaces 50. The combination of deformation and compression of the open spaces 50 results in force dissipation.

One kind of force, such as caused by a shearing action, may travel through the appliance 10 in a wave or waves. The waves may travel along an outer surface of the appliance 10 and/or through the appliance 10.

Another kind of force is a force that is normal to the appliance 10. The normal force can be applied substantially at once, it can be repeated, and/or it can increase or decrease in intensity.

While FIG. 8 depicts the two open spaces 50 both deformed to dissipate a force, it can be appreciated that only one or the other might be deformed. Further, while FIG. 8 depicts the open spaces 50 deformed into oval cross-sections, they may be deformed into other shapes and/or the shapes do not have to match one another.

The open spaces 50 are located in the appliance 10 to maximize tensile strength of the appliance 10 without exposing any of the protected dental surfaces to the unprotected teeth on the opposite jaw. The locations of the open spaces 50 also optimize saliva flow around the dentitions, which improves comfort. More particularly, saliva can be sucked through the open spaces 50. The open spaces 50 also function to improve breathing by allowing the appliance 10 to be thinner and thus take up less space in the mouth.

Based on the foregoing, it can be appreciated that the appliance material, the location of that material on the wearer's dentition as described herein, the open spaces, and/or plastic and/or elastic deformation effectively diminishes forces transmitted in the axial (normal) direction, as well as in the horizontal direction, with respect to the dental surfaces.

In accordance with the provisions of the patent statutes, the present invention has been described in what is considered to represent its preferred embodiments. However, it should be noted that the invention can be practiced otherwise than as specifically illustrated and described without departing from its spirit or scope.

What is claimed is:

1. A method of using a dental appliance, comprising:

providing a first front flap and a second front flap, a first inner side flap and a second inner side flap and an arch-shaped bite line wall connecting the first front flap and the second front flap with the first inner side flap and the second inner side flap;

locating a movable shear thickening fluid comprised of a suspension of nanoparticles inside a polymer matrix within at least one pocket fixed and entirely encased within only said first front flap and said second front flap, said pocket comprised of a channel in fluid communication with a first reservoir and a second reservoir, wherein said channel has a circular cross section and said reservoirs have circular cross-sections, wherein the channel cross section is smaller than the cross sections of the reservoirs;

dissipating a force applied to said first front flap or said second front flap by absorbing said force via a stiffening of said moveable shear thickening fluid in said channel upon receipt of said force; and relaxing said stiffened moveable shear thickening fluid after said force is dissipated to return said moveable shear thickening fluid to a non-shear thickened state.

2. The method of claim 1, wherein said nanoparticles within said moveable shear thickening fluid are subject to shear forces upon the application of the force.

3. The method of claim 2, wherein said shear forces consume energy from said force.

4. The method of claim 2, wherein said shear forces increase a viscosity of said moveable shear thickening fluid.

5. The method of claim 1, wherein said stiffening directs said force away from dentition.

6. The method of claim 1, further comprising tuning said moveable shear thickening fluid to impact forces by varying at least one of a diameter of said nanoparticles, a surface structure of said nanoparticles, a chemical functionality of said nanoparticles and electrostatic charges on said nanoparticles.

* * * * *